United States Patent
Solem

(10) Patent No.: US 6,626,914 B2
(45) Date of Patent: Sep. 30, 2003

(54) GRAFT CONNECTOR, AN INTRODUCER THEREFOR AND A METHOD OF MAKING A BRANCH CONNECTION

(75) Inventor: Jan Otto Solem, Stetten (CH)

(73) Assignee: Jomed N.V., Amsterdam (NL)

( * ) Notice: Subject to any disclaimer, the term of this patent is extended or adjusted under 35 U.S.C. 154(b) by 138 days.

(21) Appl. No.: 09/777,716

(22) Filed: Feb. 7, 2001

(65) Prior Publication Data

US 2003/0060837 A1 Mar. 27, 2003

Related U.S. Application Data

(63) Continuation of application No. PCT/SE00/01610, filed on Aug. 23, 2000, and a continuation-in-part of application No. 09/192,895, filed on Nov. 17, 1998, now Pat. No. 6,210,430.

(30) Foreign Application Priority Data

May 17, 1996 (CH) .............................. 9601884
Aug. 25, 1999 (CH) .............................. 9902991

(51) Int. Cl.[7] .................................................. A61F 11/00
(52) U.S. Cl. ...................................................... 606/108
(58) Field of Search ................................. 606/108, 148, 606/153, 215, 216, 233

(56) References Cited

U.S. PATENT DOCUMENTS

| | | |
|---|---|---|
| 5,304,220 A | 4/1994 | Maginot |
| 5,443,497 A | 8/1995 | Venbrux |
| 5,456,712 A | 10/1995 | Maginot |
| 5,571,167 A | 11/1996 | Maginot |
| 5,643,340 A | 7/1997 | Nunokawa |
| 5,755,778 A | 5/1998 | Kleshinski |
| 5,893,886 A | 4/1999 | Zegdi et al. |
| 5,925,054 A | 7/1999 | Taylor et al. |
| 6,068,654 A | 5/2000 | Berg et al. |
| 6,296,648 B1 * | 10/2001 | Boche et al. ............... 606/148 |

FOREIGN PATENT DOCUMENTS

| | | |
|---|---|---|
| WO | 88/06865 | 9/1988 |
| WO | 97/43961 | 11/1997 |

* cited by examiner

Primary Examiner—David J. Isabella
(74) Attorney, Agent, or Firm—Browdy and Neimark, P.L.L.C.

(57) ABSTRACT

A graft connector comprises a sleeve (10) and a collar (11). The sleeve (19 has an opening (12) in its circumferential surface and comprises a memory material. The collar (11) consists of a fluid-tight material and is fixed to the sleeve (10) before use of the graft connector. The collar has a shoulder portion (13) extending at least around the opening (12) and a neck portion (14) integral with the shoulder portion (13) and projecting radially from the opening (12). An introducer for the graft connector comprises two L-shaped elements (18, 19), and first releasable means (20, 21, 28–30) for locking the two L-shaped elements (18, 19) together so as to form a T-shaped element (26) having a stem (27) and two oppositely directed arms (24, 25). Removable means (31; 42; 46) are provided for temporarily reducing the diameter of the sleeve (10) during insertion into a blood vessel (2) and also for connecting the arms (24, 25) of the T-shaped element (26) along the sleeve (10) of the graft connector. The sleeve (10) is introduced into the blood vessel (2) through the longitudinal incision made therein by manipulation of the stem (27) of the T-shaped element (26). Then the two L-shaped elements (18, 19) are released from each other and from the sleeve (10) and finally they are retracted from the blood vessel (2).

7 Claims, 6 Drawing Sheets

GRAFT CONNECTOR, AN INTRODUCER THEREFOR AND A METHOD OF MAKING A BRANCH CONNECTION

This is a continuation of copending parent application No. PCT/SE00/01610, filed Aug. 23, 2000.

And is a CIP of parent application Ser. No. 09/192,895, filed Nov. 17, 1998, now U.S. Pat. No. 6,210,430.

The present invention relates generally to the field of vascular surgery and, more specifically, to a branching device or a graft connector for blood vessels, especially for bypass operations on the coronary vessels. The invention is also related to an instrument for introducing the graft connector into a blood vessel and further to a combination of a graft connector and an introducer. Further, the invention relates to a method of making a branch connection to a blood vessel.

An increased flow resistance in the various coronary vessels can jeopardise the oxygen supply to the cardiac muscle. In some cases an expansion of vascular stenosis is possible. If the flow of blood in a vessel is completely or practically completely blocked, the only thing to be done is to bypass the blocked portion to prevent an irreparable injury from arising. Such a bypass operation is usually effected by connecting a new vessel after the blocked point and connecting it to another blood vessel, for instance the aorta, which may give a sufficient flow of blood to the blood vessel after the blocked point.

In practice, such a bypass operation requires the use of a heart-lung machine, i.e. that the heart be temporarily stopped since the bypass operation when connecting, for instance, the two vessels involved requires the heart to be immovable. In consequence of the connecting technique employed and the use of the heart-lung machine, the operation will be relatively time-consuming and not completely without risk.

When larger vessels are involved, it is known from e.g. U.S. Pat. No. 5,456,712 to provide a branch by blocking the vessel by means of balloons on each side of the intended branch point, whereupon an incision is made in the blocked portion of the blood vessel. Then an expanded end of a vascular prosthesis is inserted through the incision and a stent is inserted through the one blocking balloon to a position inside the incision, where finally the stent is expanded by means of a further balloon positioned inside the stent. For completely safe fixing of the expanded end to the area around the incision in the vessel, some sort of suture is used, primarily for connecting the expanded end of the vascular prosthesis with the blood vessel around the incision therein.

This prior-art technique implies that a blocking can be made on each side of the intended branch point, and that the stent can be inserted via the diseased vessel involved and through one of the blocking balloons. In practice, also a fixing of the expanded end of the vascular prosthesis relative to the vessel involved by means of some sort of suture is required.

The technique according to U.S. Pat. No. 5,456,712 is thus not suited for use in thin vessels, such as the coronary vessels, or in other positions where the described blocking by means of a balloon from the inside of the vessel is not possible.

A more a simple and reliable bypass of the coronary vessels without necessitating temporary internal blockings is disclosed as a branching device in WO97/43961. This branching device has a sleeve, which is radially extensible and has an opening in its circumferential surface, and a collar which consists of a fluid-tight material and is fixed to the sleeve before the branching device is used and which has, on the one hand, a shoulder portion extending at least around the opening in the circumferential surface of the sleeve and, on the other hand, a neck portion integral with the shoulder portion and projecting radially from the opening in the circumferential surface of the sleeve.

The opening in the circumferential surface of the sleeve is preferably arranged unsymmetrically relative to the ends of the sleeve. This confers an advantage since the necessary longitudinal incision in the blocked vessel need not be made longer than the distance from the neck portion to the nearest end of the sleeve, while the sleeve of the branching device can be retained safely in the vessel thanks to the sleeve obtaining a long part (seen from the neck portion), which must thus first be inserted into the opening in the vessel.

After the insertion of the sleeve into the vessel in a reciprocating movement, the short part of the sleeve is positioned completely beyond the opening in the vessel, while the long part of the sleeve covers the main part of the opening in the vessel and besides can extend beyond this a distance of essentially the same length as the short part of the sleeve. Once the sleeve is correctly positioned in the vessel, its position is to be fixed. This is possible according to WO97/43961 thanks to the sleeve being radially extensible by means of a balloon and retaining its extended shape, i.e. the shape of the sleeve is permanently deformable. This results in an expansion of the vessel, which then clamps the sleeve in place and also clamps the shoulder portion of the collar against the sleeve.

An object of the present invention is to further improve the branching device disclosed in WO97/43961 and especially improve and simplify the insertion of a graft connector into a blood vessel.

This object is achieved by a graft connector having the features according to the accompanying claim 1, by an introducer having the features according to the accompanying claim 16, and by a combination having the features according to the accompanying claim 23. Also, the object is achieved by a method having the features according to any one of the accompanying claims 24–26.

Thus, the graft connector comprises a sleeve, which has an opening in its circumferential surface and comprises a memory material, a collar which consists of a fluid-tight material and is fixed to the sleeve before use of the graft connector and which has, on the one hand, a shoulder portion extending at least around the opening in the circumferential surface of the sleeve and, on the other hand, a neck portion integral with the shoulder portion and projecting radially from the opening in the circumferential surface of the sleeve, and removable means for temporarily reducing the diameter of the sleeve during insertion into a blood vessel.

The removable means may comprise a suture encircling at least part of the sleeve and thereby reducing the diameter of the sleeve.

Further, the graft connector may comprise edge means for cutting the suture once the sleeve is introduced into the blood vessel.

Preferably, the edge means comprises a needle having an edged hole at a tip thereof, through which hole the suture is extending.

Further, the graft may comprise two L-shaped elements, first releasable means for locking the two L-shaped elements together so as to form a T-shaped element having a stem and two oppositely directed arms, and second releasable means for connecting the arms of the T-shaped element along the sleeve of the graft connector. Thereby, the sleeve may be introduced into the blood vessel through the longitudinal incision made therein by manipulation of the stem of the T-shaped element and the two L-shaped elements may be released from each other and from the sleeve and then retracted from the blood vessel.

The suture should encircle at least part of the sleeve and the arms of the T-shaped element, which may have a longitudinal channel in which the needle is positioned.

The needle should be retractable from the longitudinal channel of the T-shaped element. Also, a cap may enclose the free ends of the stem in its non-retracted position. Further, the needle and the cap are locking the two L-shaped elements to each other.

According to the present invention, an introducer is provided for a T-shaped graft connector, which comprises a sleeve that is to be introduced into a blood vessel through a longitudinal incision made therein, the sleeve having an opening in its circumferential surface, and a collar adjoining the opening and extending radially therefrom and, when the sleeve is introduced into the blood vessel, extending out from the longitudinal incision made therein.

This introducer comprises two L-shaped elements, first releasable means for locking the two L-shaped elements together so as to form a T-shaped element having a stem and two oppositely directed arms, and second releasable means for connecting the arms of the T-shaped element along the sleeve of the graft connector, whereby the sleeve may be introduced into the blood vessel through the longitudinal incision made therein by manipulation of the stem of the T-shaped element and the two L-shaped elements may be released from each other and from the sleeve and then retracted from the blood vessel.

In such an introducer, the second releasable means for connecting the sleeve of the graft connector in parallel with the arms of the T-shaped element may comprise a suture encircling at least part of the sleeve and the arms of the T-shaped element.

Further, the second releasable means for connecting the sleeve of the graft connector in parallel with the arms of the T-shaped element may comprise an edge for cutting the suture.

More precisely, the second releasable means for connecting the sleeve of the graft connector in parallel with the arms of the T-shaped element may comprise a needle having an edged hole at a tip thereof, through which hole the suture is extending. The T-shaped element may have a longitudinal channel in which the needle is positioned.

Preferably, the needle is retractable from the longitudinal channel of the T-shaped element and has a cap enclosing the free ends of the stem in its non-retracted position. Also, the needle and the cap may lock the two L-shaped elements to each other.

According to the invention, a method of connecting the above described T-shaped graft connector to a blood vessel comprises the steps of locking the T-shaped element to the sleeve, reducing the diameter of the sleeve, making a longitudinal incision in the blood vessel, inserting the sleeve through the incision into the blood vessel using the stem as a holder, the collar extending radially out of the incision in the blood vessel, releasing the sleeve from the T-shaped element to allow the sleeve to expand within the vessel, and removing the T-shaped element from the blood vessel.

As an alternative, a method of making a branch connection to a blood vessel using the T-shaped graft connector and the T-shaped element comprises the steps of locking the T-shaped element to the sleeve such that the sleeve extends along the arms and the collar extends substantially along the stem, reducing the diameter of the sleeve, making a longitudinal incision in the blood vessel, inserting the sleeve through the incision into the blood vessel using the stem as a holder, the collar extending radially out of the incision in the blood vessel, releasing the sleeve from the T-shaped element to allow the sleeve to expand within the vessel, and removing the T-shaped element from the blood vessel.

Preferably, the T-shaped graft connector and the T-shaped element are already releasably locked to each other when delivered for introduction into a blood vessel. Then the method for making a branch connection to a blood vessel comprises the steps of making a longitudinal incision in the blood vessel, inserting the sleeve and the arms of the T-shaped element through the incision into the blood vessel using the stem as a holder, the collar extending radially out of the incision in the blood vessel, releasing the sleeve from the T-shaped element to allow the sleeve to expand within the vessel, and removing the T-shaped element from the blood vessel.

The locking of the T-shaped element to the sleeve may comprise at least partly encircling the sleeve and the arms with a suture, which may be released from the T-shaped element by cutting.

Alternatively, the locking of the T-shaped element to the sleeve may comprise inserting each one of the arms and an adjoining part of the sleeve into a tube made of a plastic film, e.g. made from PTFE, and then shrinking the tube thereby also reducing the diameter of the sleeve, which may be released from the T-shaped element by a longitudinal cut through the tube.

As a further alternative, the locking of the T-shaped element to the sleeve may comprise making a tube of each one of the arms and a sheet of a plastic film, said tube encircling an adjoining part of the sleeve, and reducing the diameter of the sleeve. Here, the diameter of the tube may be reduced by shrinking of the plastic film when the tube is made, whereby the diameter of the sleeve is reduced, or the diameter of the sleeve may be reduced at the same time as the tube is made.

The invention will now be described in more detail with reference to the accompanying drawings, in which FIG. 1 is a perspective view and shows a heart with two schematically indicated bypasses of coronary vessels each having a blocking, FIG. 2 is a perspective view and shows, among other things, a few parts included in one embodiment of a graft connector according to the invention, FIG. 3 shows the parts in FIG. 2 in an assembled state before insertion into a blocked vessel, FIG. 4 is a perspective view and shows the graft connector and separated elements of an embodiment of an introducer according to the present invention, FIG. 5 is a side view and shows the graft connector and the introducer in FIG. 4 in and assembled state before insertion into a blocked vessel, FIG. 6 is an end view of the graft connector and the introducer in FIG. 5, FIG. 7 is a cross-sectional view along the lines VII—VII in FIG. 6, and FIG. 8 a cross-sectional view through the tip of a needle and partly through arms shown in 4 and illustrates a first embodiment of means for connecting the introducer to the graft connector.

Figure 1:
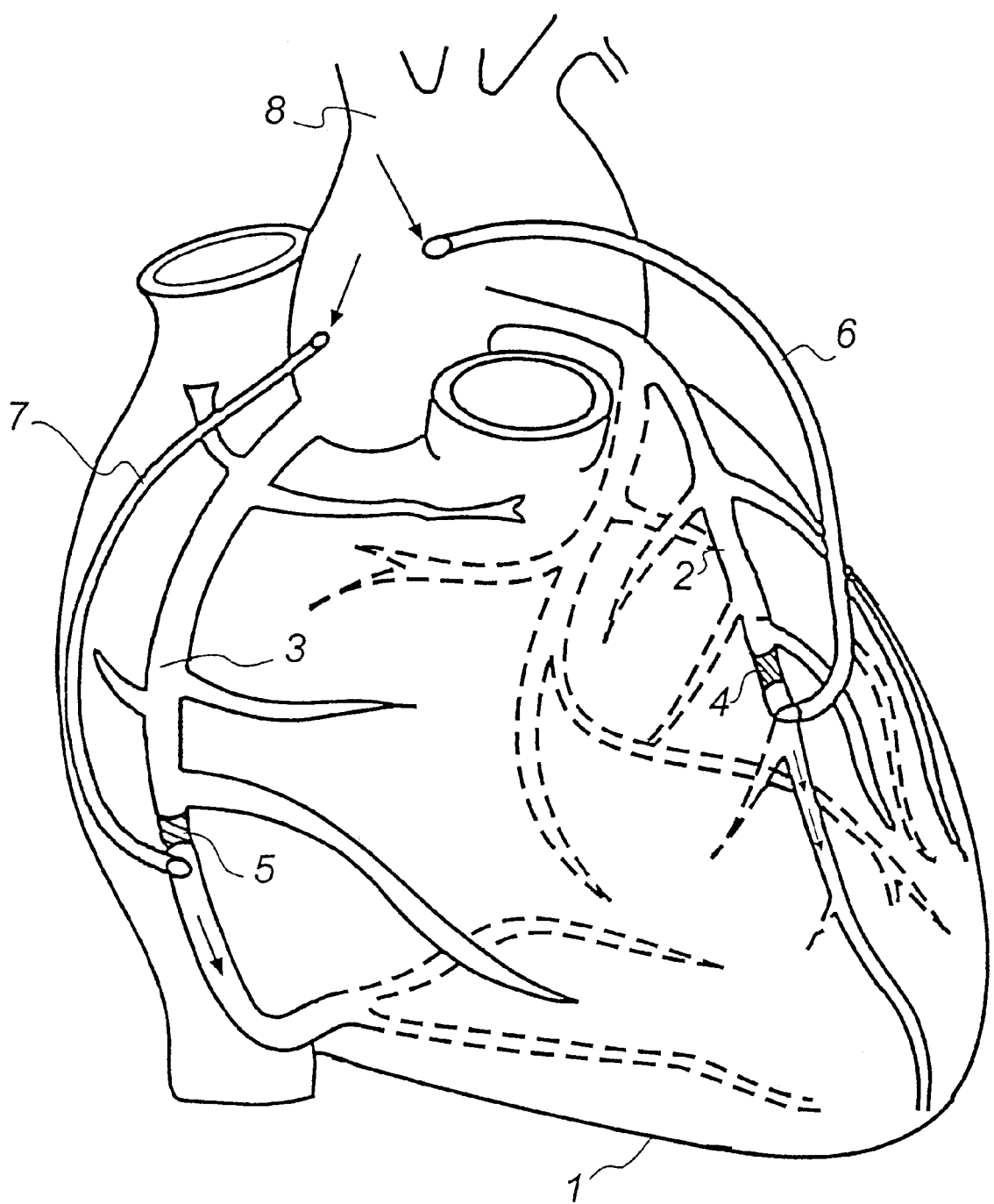

The heart 1 shown in FIG. 1 has two coronary vessels 2, 3 each having a blocking 4, 5, i.e. a stenosis or an occlusion. FIG. 1 illustrates schematically how these blockings 4, 5 are bypassed by means of two grafts or vessels 6, 7 which can be taken from the patient himself. More specifically, one end of the vessel 6 is connected after the blocking 4, seen in the normal direction of flow in the vessel 2, and its other end is connected to the aorta 8, such that a sufficient quantity of oxygen-rich blood will be supplied to the already blocked coronary vessel 2 after the blocking 4 therein. The same applies to the vessel 3.

For effecting the connection of the vessel 6 to the coronary vessel 2, the embodiment shown in FIGS. 2–8 of a graft connector or branching device according to the invention can be used. The main components of this branching device are a sleeve 10 and a collar 11 fixed thereto. The sleeve 10 consists of a memory material that is not rejected by the body tissue. Its construction is such as to have a predetermined diameter, which can be reduced by compression. When releasing the compression, the sleeve 10 will automatically expand to its predetermined, larger diameter.

A suitable material for the sleeve 10 is in the form of a net that permits said compression and expansion.

According to the invention, the sleeve 10 further has an axially elongate opening 12, whose dimensions, when the sleeve 10 expands, may be distorted in a manner similar to the distortion of the actual sleeve 10, i.e. a shortening in the axial direction and an expansion in the circumferential direction. The opening 12 may thus obtain a decreased length in the axial direction of the sleeve 10, but an increased width in the circumferential direction of the sleeve 10.

The collar 11 consists of a fluid-tight and preferably flexible or even elastic material, which of course must also be such as not to risk being rejected by the body tissue. More specifically, the collar 11 has a shoulder portion 13 and a neck portion 14.

The shoulder portion 13 has a shape substantially conforming to the shape of the sleeve 10. It has such a size as to overlap the opening 12 and thus extend over the sleeve 10 around the opening 12. The overlapping is also so great as to remain also in case of a certain change of the size of the opening 12, as will be described below. The shoulder portion 13 can also completely encompass at least part of or the entire sleeve 10, in which case the material of the shoulder portion 13 is so elastic as not to essentially counteract neither a compression nor an expansion of the sleeve 10, as will be described below. Preferably, the shoulder portion 13 completely encompasses the entire sleeve 10, as shown in FIG. 2

The neck portion 14 of the collar 11 is a direct extension of the shoulder portion 13 and essentially has the shape of a cylinder. The most important function of the neck portion 14 is to serve as connecting member for the graft or new vessel 6.

Figure 2:
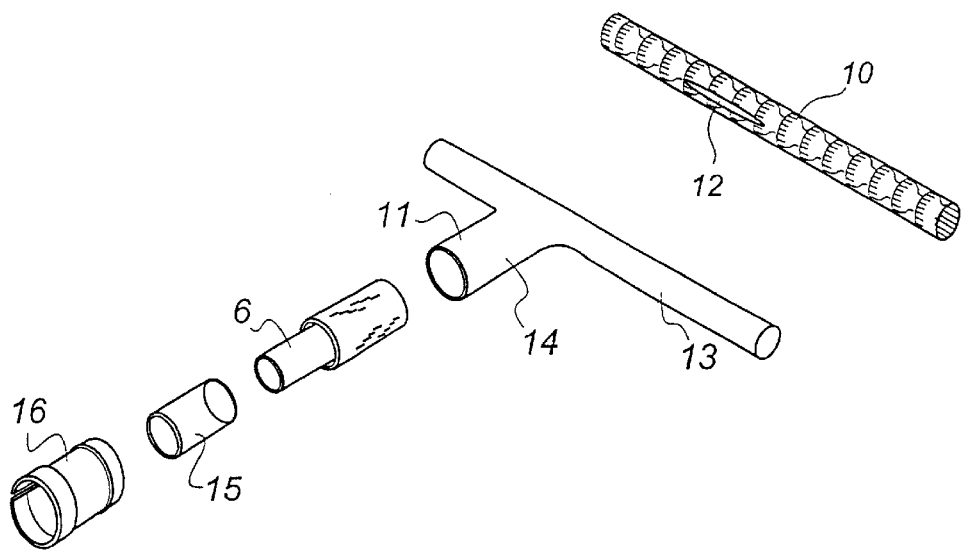
Figure 3:
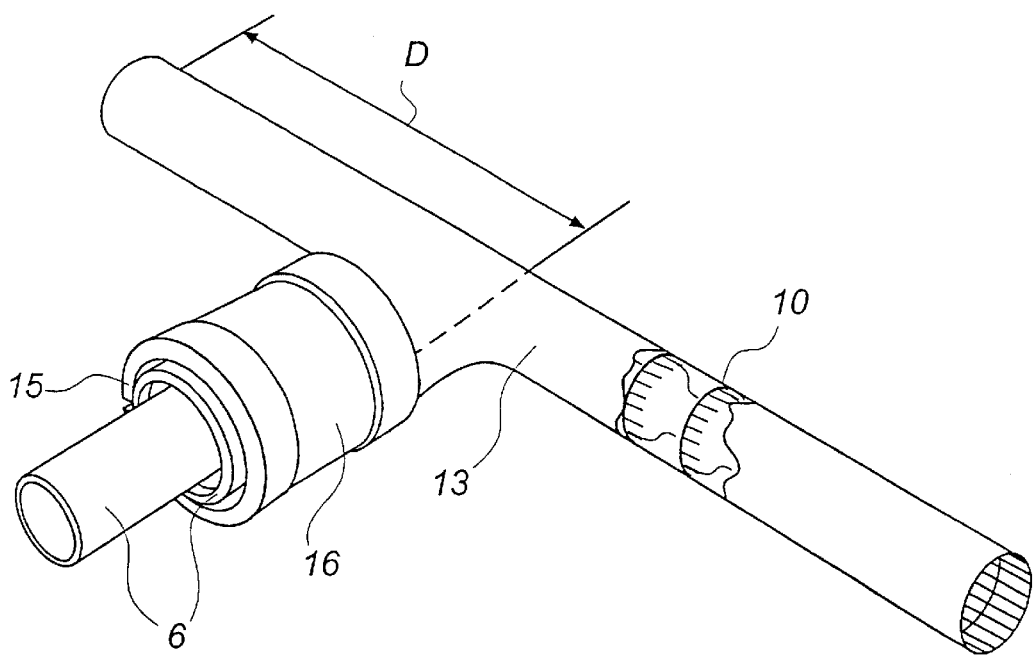

For the connection between the neck portion 14 and the vessel 6, a rigid supporting sleeve 15 and a clamping or locking sleeve 16 can be used according to the embodiment illustrated in FIGS. 2 and 3 of the drawings. The end of the vessel 6 is adapted to be inserted into and through the supporting sleeve 15, and the outermost part of the vessel 6 is then to be folded or pulled back over the outside of the supporting sleeve 15. This folding back of the end of the vessel 6 is shown in FIG. 2, but with the supporting sleeve 15 separated from the vessel 6. For completion of the connection, the supporting sleeve 15 with the pulled-on vessel 6 is inserted into the open end of the neck portion 14. Then the clamping sleeve 16 is arranged and clamped around the neck portion 14, which then together with the interiorly situated, folded-back part of the vessel 6 is pressed against the outside of the supporting sleeve 15. As a result, a fixed and tight connection between the neck portion 14 and the vessel 6 is achieved.

The actual clamping sleeve 16 may be divisible so as to be laterally movable over the neck portion 14 before the clamping operation, which suitably is effected by the clamping sleeve 16 having, at its ends that are free before clamping, hooks engaging each other and permitting an easy tightening of the clamping sleeve 16 around the neck portion 14.

For fixing the sleeve 10 and the collar 11 relative to e.g. the blood vessel 2 in FIG. 1, the sleeve 10 is made from a memory material and removable means are used for temporarily reducing the diameter of the sleeve 10 during insertion into the blood vessel 2. By releasing these removable means, the sleeve 10 can be expanded in its place within the blood vessel 2, such that the blood vessel 2 also is expanded and thus is pressed against the sleeve 10 for fixing the position thereof in the blood vessel 2. At the same time the collar 11, more precisely the shoulder portion 13, will be squeezed between the blood vessel 2 and the sleeve 10, such that the position of the collar 11 will be safely fixed relative to the blood vessel 2 and a fluid-tight seal between this and the collar 11 is obtained without necessitating any suture.

It is preferable to first prepare the connection between the collar 11 and the new vessel 6. Subsequently, the sleeve 10 can in a reciprocating movement be inserted into, for instance, the vessel 2 through an opening formed therein by a longitudinal incision. Then the branching device is fixed in the vessel 2 by release of the removable means, whereby the sleeve 10 expands.

For completion of the operation, the free end of the new vessel 6 is to be connected to a blood vessel, for instance the aorta 8, which can give a sufficient flow of blood to the vessel 2 after the blocking 4.

In an alternative method of carrying out a bypass operation by means of the graft connector according to the invention, the new vessel 6 first is connected to the blood vessel, e.g. the aorta, which can give a sufficient flow of blood, and is then connected to the vessel having a blocking.

According to a further alternative, an arterial vessel originating from the aorta or some other artery, e.g. the internal mammary artery, capable of giving a sufficient flow of blood may be used as the new vessel 6, thus requiring connection only at one end.

It should be emphasised that in the methods described above, the collar 11 is even from the beginning fixed to the sleeve 10, and that the shoulder portion 13 preferably encompasses the entire sleeve 10.

Figure 4:
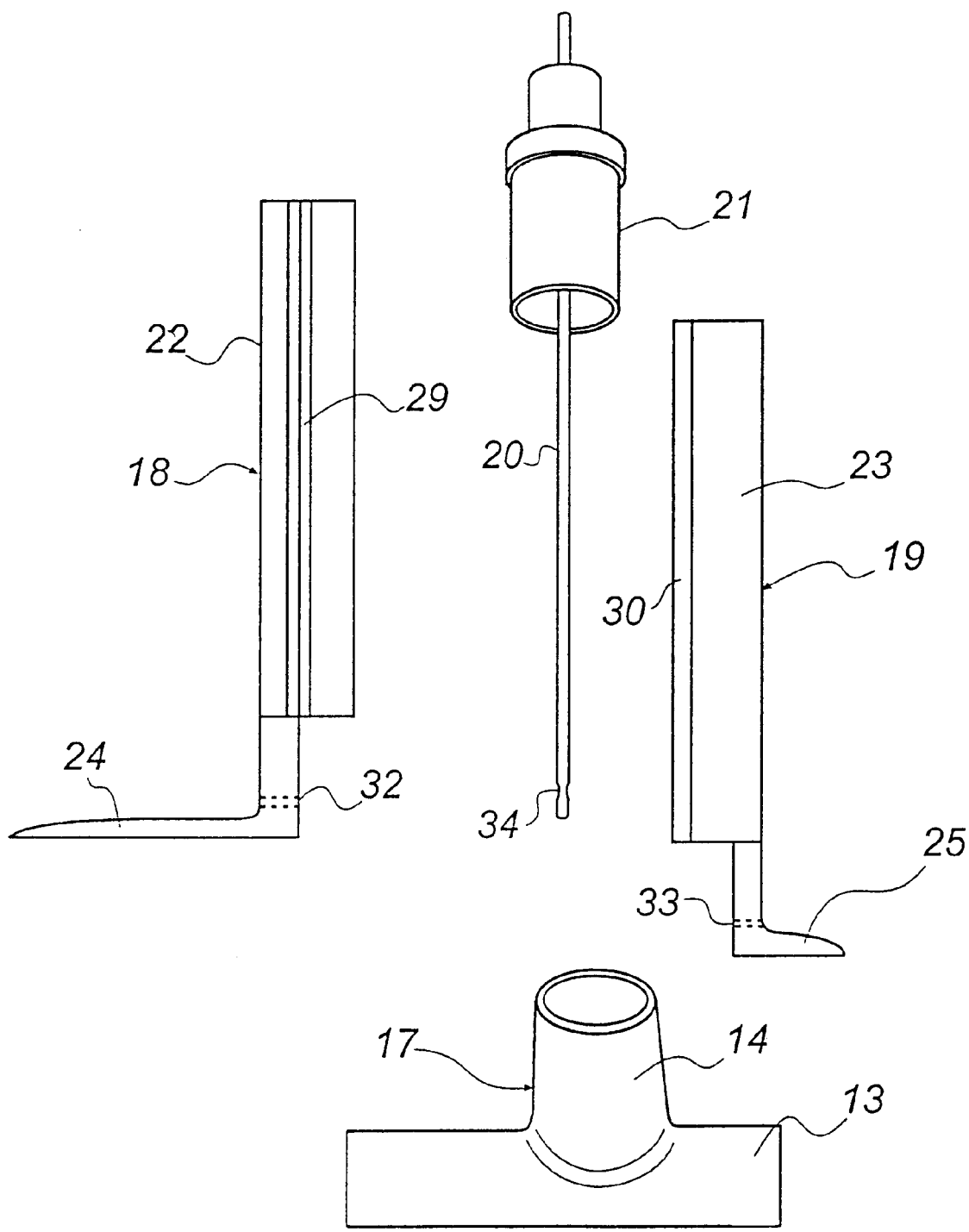
Figure 6:
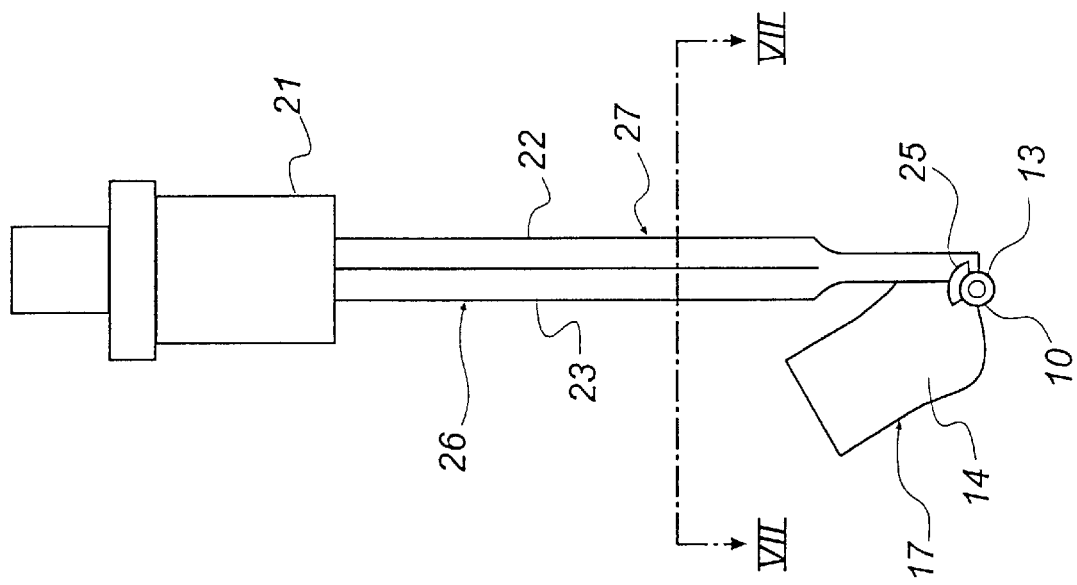
Figure 5:
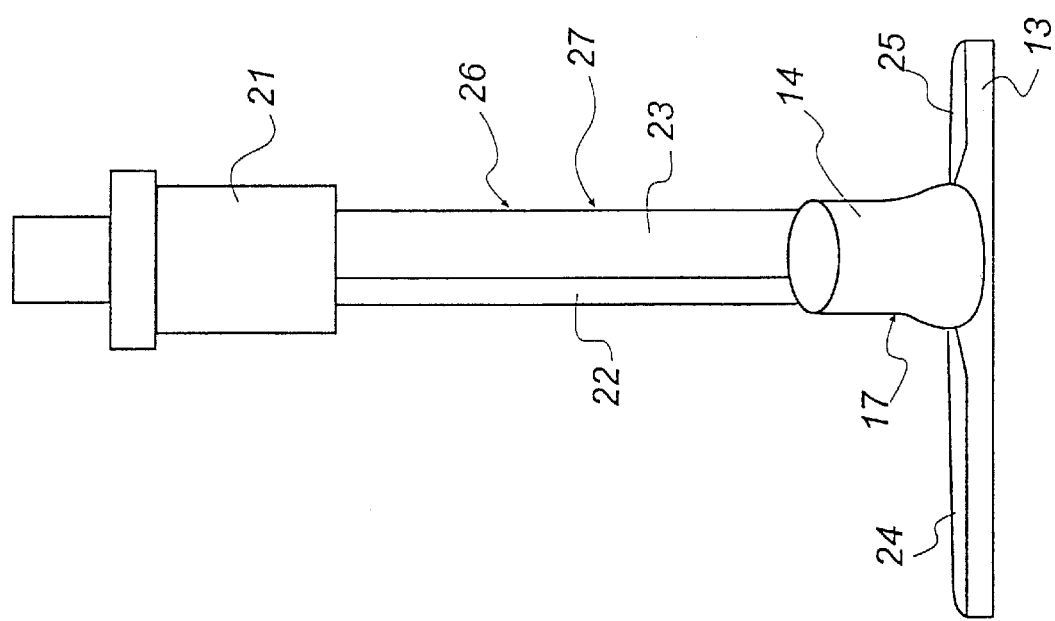

FIG. 4 shows a T-shaped graft connector 17, i.e. the elements 10–14 of FIG. 2 in an assembled state. Further, elements 18–21 of an introducer or inserter are illustrated. These elements 18–21 include two L-shaped elements 18 and 19, a tubular needle 20 and a cap 21. The L-shaped elements 18 and 19 each have a stem portion 22 and 23, respectively, and an arm 24 and 25, respectively. The arms 24 and 25 are of different length, the arm 24 being longer than the arm 25. This difference in length corresponds to the asymmetric position of the opening 12 in the sleeve 10.

The two L-shaped elements 18 and 19 may be assembled so as to form a T-shaped element 26 having a stem 27 formed by the two stem portions 22 and 23, as illustrated in FIGS.

5 and 6, and the arms 24 and 25 extending in opposite directions. The two L-shaped elements 18 and 19 may be locked in the assembled state by means of the cap 21 and the needle 20.

The locking effect of the cap 21 is obtained when the cap 21 is pushed down on the free end of the stem 27, thereby blocking the corresponding ends of the stem portions 22 and 23 from moving away from each other.

Figure 7:
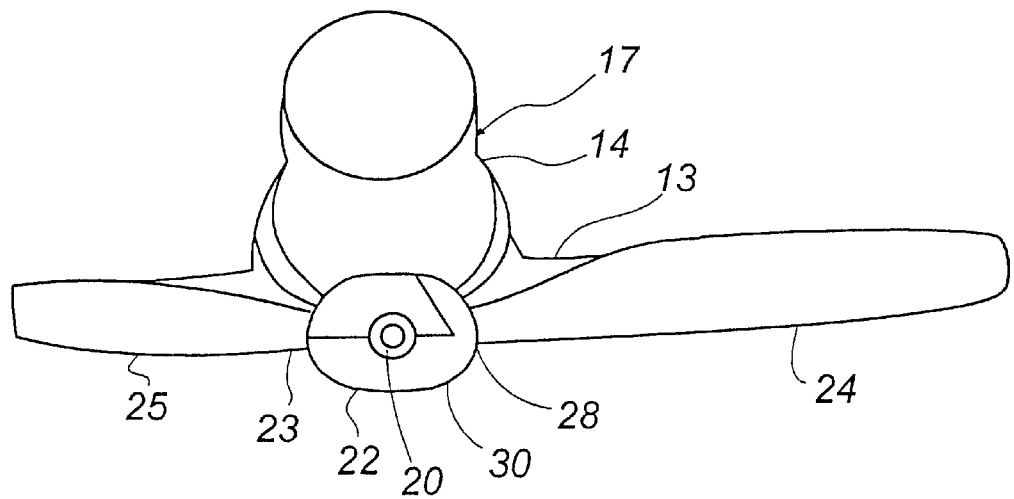

The locking effect of the needle 20 follows from the cross-sectional shape of the stem portions 22 and 23, as illustrated in FIG. 7. The stem portion 22 has a V-shaped groove 28, and the stem portion 23 has a cross-sectional profile of a shape that is complementary to the cross-sectional shape of the groove 28. A longitudinal channel 29 of circular cross-sectional shape is formed partly in the stem portion 22 and partly in the stem portion 23 so that an edge 30 of the stem portion 23 is locked in the inner corner of the groove 28, when the needle 20 is inserted into the channel 29.

In order to be able to insert the sleeve 10 into a blood vessel, in which an opening of substantially the same length as the length D in FIG. 3 is made by an incision, the sleeve 10 has to be compressed temporarily during the insertion. According to the invention, this compression is obtained by removable means, such as a suture encircling at least part of the sleeve 10 as well as the encompassing shoulder portion 13. In its compressed state, the sleeve 10 can be introduced through the incised opening in the blood vessel by a reciprocating movement leaving the neck portion 14 close to one end of the longitudinal opening in the blood vessel.

According to the present invention, the introducer or inserter is preferably used for the above described introducing of the sleeve 10 into the blood vessel in which a longitudinal incision has been made. More precisely, the L-shaped elements 18 and 19 are assembled as described above to form the T-shaped element 26 and then the sleeve 10 is compressed and connected along the arms 24 and 25 of the T-shaped element 26. This connection is made by second releasable means such that the arms 24 and 25 may be released from the sleeve 10 when the sleeve 10 is inserted into the blood vessel and correctly positioned therein. The compression of the sleeve 10 should preferably be suspended substantially at the same time, such that the sleeve 10 expands and assumes a fixed position in the blood vessel.

When the arms 24 and 25 are released from the sleeve 10, they may be released from each other. They are then easily removed from the blood vessel one at a time.

Figure 8:
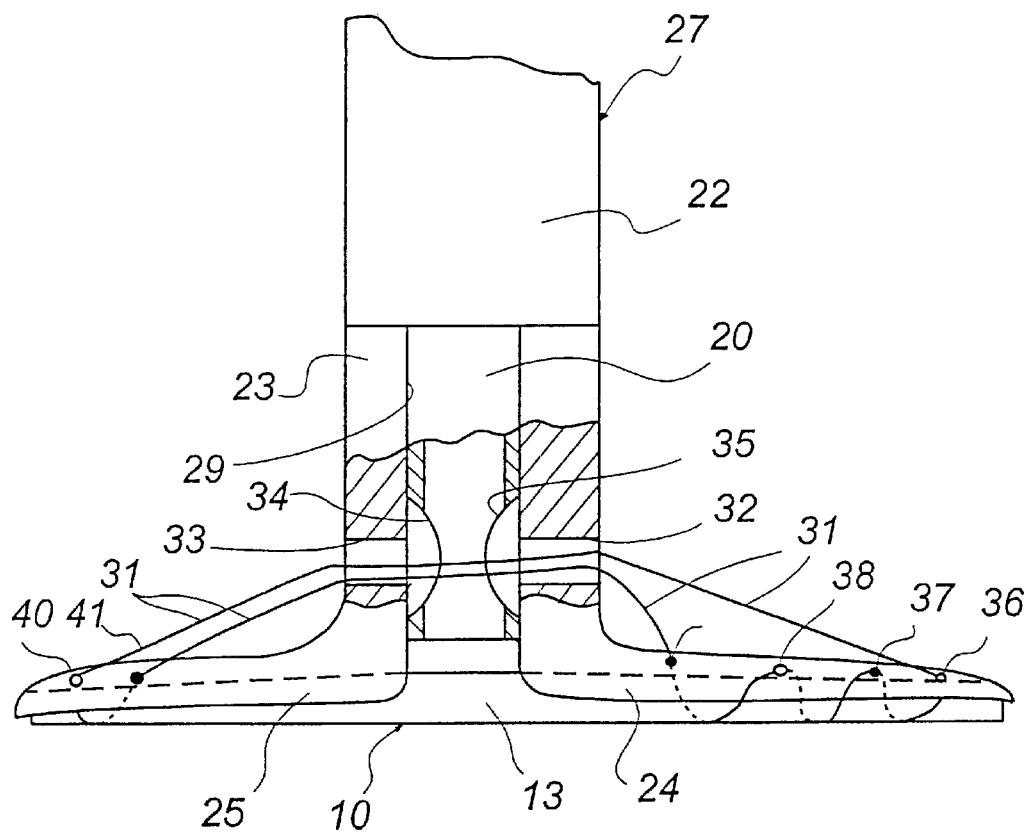

The compression of the sleeve 10 and the encompassing shoulder portion 13 may be made by a suture 31, shown in FIG. 8. This suture 31 is wound around the sleeve 10 and the shoulder portion 13 so as to encircle at least part thereof and thereby reduce the diameter of the sleeve 10. Further, it is advantageous to use the same suture 31 for connecting the sleeve 10 to the arms 24 and 25, such that by cutting the suture 31 by means of an edge means the arms 24 and 25 will be released from the sleeve 10 and the memory material of the sleeve 10 will be allowed to expand the sleeve 10 to the predetermined diameter.

The needle 20 is used for cutting the suture 31. More precisely, the suture 31 is guided through holes 32 and 33 extending through the stem portions 22 and 23 close to the arms 24 and 25. The needle 20 has corresponding holes 34 at its tip receiving the suture 31, which extends, preferably twice, between the holes 32 and 33. The holes 34 are edged each having a sharp edge 35 such that when the needle 20 is moved out from the channel 29 in the stem 27, the suture 31 will be cut. The suture 31 would also be cut by a twisting movement of the needle 20 in the channel 29 in the stem 27.

As shown in FIG. 8, the arms 24 and 25 each have a series of holes 36–39 and 40–41, respectively, distributed lengthwise from the tip thereof. The holes 36, 37 and 40, 41 are used to ensure that the suture 31 makes at least one turn around the sleeve 10 close to the tip of each one of the arms 24 and 25, and consequently close to the ends of the sleeve 10. More precisely, the suture 31 may follow a path from the hole 32 to the hole 36 most close to the tip of the arm 24, down through this hole 36, around the compressed sleeve 10 and in between the arm 24 and the sleeve 10 to the hole 37 next to the hole 36, up through this hole 37, around the compressed sleeve 10 and in between the arm 24 and the sleeve 10 to the hole 38 next to the hole 37, up through this hole 38, around the compressed sleeve 10 and in between the arm 24 and the sleeve 10 to the hole 39 next to the hole 38, up through this hole 39, around the compressed sleeve 10 and back to and through the hole 32 in the stem portion 22. The suture 31 then passes through the hole 34 in the needle 20 and the hole 33 in the stem portion 23 to the hole 40 close to the tip of the arm 25, down through this hole 40, around the compressed sleeve 10 and in between the arm 25 and the sleeve 10 to the hole 41 next to the hole 40, up through this hole 40, around the compressed sleeve 10 and back to and through the hole 33 in the stem portion 23 and the hole 34 in the needle 20.

Thereby, the suture 31 forms an endless loop connecting the arms 24, 25 of the T-shaped element 26 to the sleeve 10 and also compressing the sleeve 10.

It should be noted that the suture 31 may be guided along other paths through the holes 32, 33, 34, 36–39, 40 and 41. Preferably, the suture 31 should not make a complete turn around both the sleeve 10 and the arm 24 or 25, since that may jeopardize a final removal of the suture 31.

The suture 31 represents a first embodiment of removable means for temporarily reducing the diameter of the sleeve during insertion into a blood vessel. The suture 31 also constitutes second releasable means for connecting the arms of the T-shaped element 26 along the sleeve 13 of the graft connector. Of course, separate sutures could be used as said removable means and said second releasable means.

Figure 9:
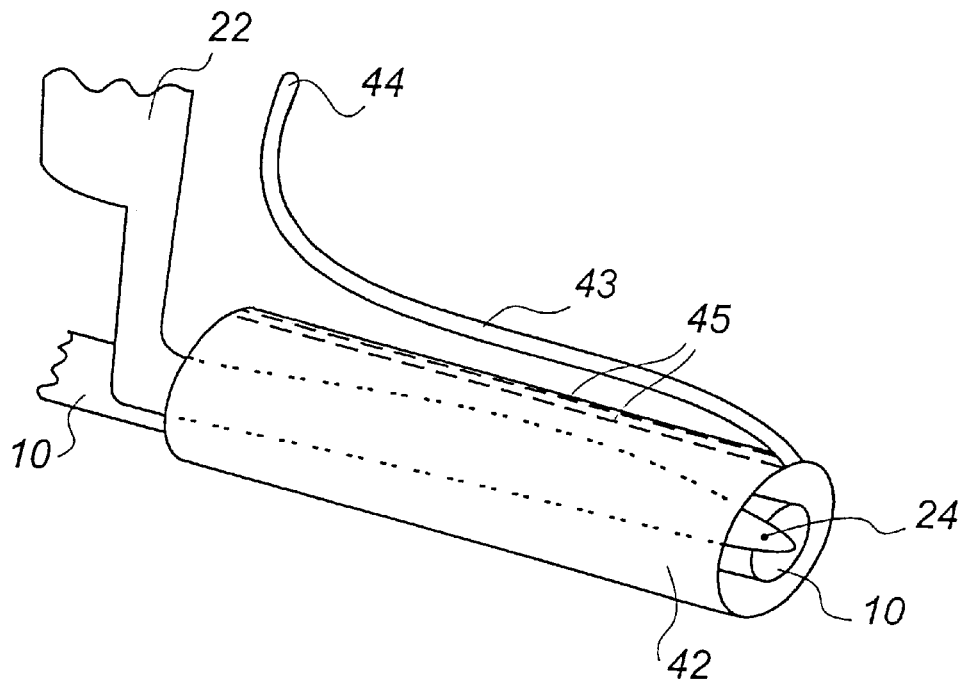
FIG. 9 is as schematic view illustrating a second embodiment of means for connecting the introducer to the graft connector.

A second embodiment of said removable means and said second releasable means is illustrated in FIG. 9 and comprises a tube 42 made of a film material, preferably a plastic film, e.g. a PTFE-film. This tube 42 is pushed in over the arm 24 and an adjoining part of the sleeve 10 (as shown) and then is shrinked, whereby the sleeve 10 is compressed (as is the encompassing shoulder portion 13) and also is connected to the arm 24. A corresponding tube (not shown) is used for connecting the arm 25 to an adjoining part of the sleeve 10 and compressing this part of the sleeve 10. In order to release the sleeve 10 from the arms 24, 25, the tube 42 has a strip 43, which has a free end 44 and is folded back over the tube 42 along perforations 45. By pulling the strip 43 by its free end 44, the tube 42 is opened along the perforations 45, such that the opened tube 42 may be removed. As a consequence of the opening, the sleeve 10 is released from the arms 24, 25 and is allowed to expand.

Figure 10:
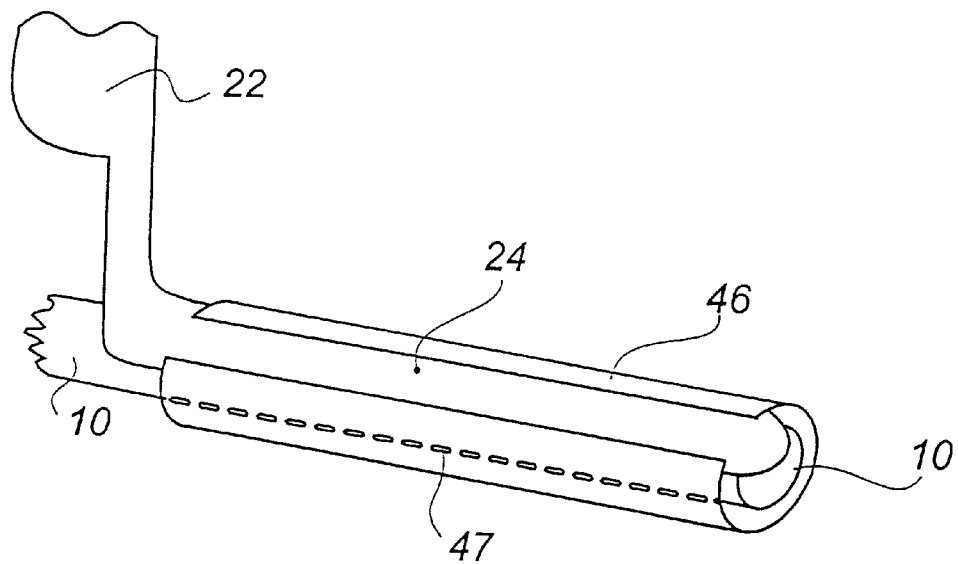
FIG. 10 is as schematic view illustrating a third embodiment of means for connecting the introducer to the graft connector.

A third embodiment of said removable means and said second releasable means is illustrated in FIG. 10 and comprises a substantially rectangular film sheet 46 which is connected to the longitudinal edges of the arm 24 such that the arm 24 and the film sheet 46 forms a tube enclosing the adjoing part of the sleeve 10 (as well as the corresponding part of the encompassing shoulder portion 13). A corresponding film sheet (not shown) is to be used for the arm 25 and the adjoining part of the sleeve 10. The film sheet 46 may be shrinked so as to compress the adjoining part of the sleeve 10 and connect this part to the arm 24.

Alternatively, an edge of the film sheet 46 may be fixed to one of the longitudinal edges of the arm 24. Then, the film sheet 46 is wrapped around the sleeve 10 and fixed to the other longitudinal edge of the arm 24. Preferably, the sleeve 10 is compressed at the same time, but alternatively the film sheet 46 may be shrinked afterwards.

The film sheet 46 may be released from compressing the sleeve 10 by means of a longitudinal perforation 47, the release being initiated by a pulling force being applied to the L-shaped element 18 when withdrawing the arm 24 from within the vessel, e.g. the coranary vessel 2.

Alternatively, the film sheet 46 could have a releasable connection to one of the longitudial edges of the arm 24.

The expert realises that several modifications of the above-described embodiments of the graft connector and the introducer or inserter are conceivable within the scope of the invention as defined in the appended claims.

What is claimed is:

1. An introducer for a T-shaped graft connector, said graft connector comprising
    a sleeve (10) that is to be introduced into a blood vessel (2) through a longitudinal incision made therein, the sleeve (10) having an opening (12) in a circumferential surface thereof, and
    a collar (11) adjoining the opening (12) and extending radially therefrom and, when the sleeve (10) is introduced into the blood vessel (2), extending out from the longitudinal incision made therein,
    the introducer comprising
        two L-shaped elements (18, 19);
        first releasable means (20, 21, 28–30) for disconnectably locking the two L-shaped elements (18, 19) together so as to form a T-shaped element (26) having a stem (17) and two oppositely directed arms (24, 25); and
        second releasable means (31; 42; 46) for connecting the arms (24, 25) of the T-shaped element (26) along the sleeve (10) of the graft connector,
        whereby the sleeve (10) may be introduced into the blood vessel (2) through the longitudinal incision made therein by manipulation of the stem (17) of the T-shaped element (16) and the two L-shaped elements (18, 19) may be release from each other and from the sleeve (10) and then retracted from the blood vessel (2).

2. An introducer as claimed in claim 1, wherein the second releasable means (31; 42; 46) for connecting the sleeve (10) of the graft connector in parallel with the arms (24, 25) of the T-shaped element (26) comprises a suture (31) encircling at least part of the sleeve (10) and the arms (24, 25) of the T-shaped element (26).

3. An introducer as claimed in claim 2, wherein the second releasable means (31; 42; 46) for connecting the sleeve (10) of the graft connector in parallel with the arms (24, 25) of the T-shaped element (26) comprises an edge (35) for cutting the suture (31).

4. An introducer as claimed in claim 3, wherein the second releasable means for connecting the sleeve (10) of the graft connector in parallel with the arms (24, 25) of the T-shaped element (26) comprises a needle (20) having an edged hole (34, 35) at a tip thereof, through which hole (34) the suture (31) is extending.

5. An introducer as claimed in claim 4, wherein the T-shaped element (26) has a longitudinal channel (29) in which the needle (20) is positioned.

6. An introducer as claimed in claim 5, wherein the needle (20) is retractable from the longitudinal channel (29) of the T-shaped element (26) and has a cap (21) enclosing the free ends of the stem in a non-retracted position of the needle.

7. An introducer as claimed in claim 6, wherein the needle (20) and the cap (21) locks the two L-shaped elements (18, 19) to each other by the needle locking an edge (30) of a stem portion (23) of one of the L-shaped elements (19) in a groove (28) of a stem portion (22) of the other of the L-shaped elements (19), and the cap (21) enclosing the free ends of the stem portions (22, 23) of the two L-shaped elements (18, 19).

* * * * *